US008527061B2

(12) United States Patent
Ker et al.

(10) Patent No.: US 8,527,061 B2
(45) Date of Patent: Sep. 3, 2013

(54) LOAD-ADAPTIVE BIOELECTRIC CURRENT STIMULATOR

(75) Inventors: Ming-Dou Ker, Hsinchu County (TW); Wei-Ling Chen, Taipei (TW); Chun-Yu Lin, Hualien County (TW)

(73) Assignee: National Chiao Tung University, Hsinchu (TW)

( * ) Notice: Subject to any disclaimer, the term of this patent is extended or adjusted under 35 U.S.C. 154(b) by 106 days.

(21) Appl. No.: 13/224,166

(22) Filed: Sep. 1, 2011

(65) Prior Publication Data

US 2012/0290046 A1    Nov. 15, 2012

(30) Foreign Application Priority Data

May 13, 2011 (TW) .............................. 100116827 A (51) Int. Cl.
*A61N 1/08* (2006.01)
(52) U.S. Cl.
USPC ................... 607/62; 607/55; 607/56; 607/57; 607/63; 607/64
(58) Field of Classification Search
USPC ....................................................... 607/1–76
See application file for complete search history.

(56) References Cited

U.S. PATENT DOCUMENTS

| | | | |
|---|---|---|---|
| 4,612,934 A * | 9/1986 | Borkan ............................ | 607/62 |
| 5,350,407 A | 9/1994 | McClure et al. | |
| 5,895,416 A * | 4/1999 | Barreras et al. .................. | 607/62 |
| 6,289,246 B1 * | 9/2001 | Money ............................. | 607/56 |
| 6,647,290 B2 * | 11/2003 | Wuthrich ......................... | 607/5 |
| 6,822,884 B1 * | 11/2004 | Rosenthal et al. .............. | 363/59 |
| 2009/0132009 A1 * | 5/2009 | Torgerson ....................... | 607/61 |

FOREIGN PATENT DOCUMENTS

| | | |
|---|---|---|
| TW | I306407 | 2/2009 |
| TW | I329027 | 8/2010 |

OTHER PUBLICATIONS

Chen, et al. "An Integrated 256-Channel Epiretinal Prosthesis" IEEE Journal of Solid-State Circuits, (Sep. 2010) pp. 1946-1956, vol. 45, No. 9.

Dommel, et al. "A CMOS Retinal Neurostimulator Capable of Focussed, Simultaneous Stimulation", Journal of Neural Engineering, (May 2009), vol. 6., No. 3.

Liu, et al. "An Integrated Implantable Stimulator That Is Fail-Safe Without Off-Chip Blocking Capacitors", IEEE Transactions on BioMedical Circuits and Systems, (Sep. 2008), pp. 231-244, vol. 2, No. 3.

Sivaprakasam, et al. "Architecture Tradeoffs in High-Density Microstimulators for Retinal Prosthesis" IEEE Transactions on Circuits and Systems—I: Regular Papers, (Dec. 2005), pp. 2629-2641, vol. 52, No. 12.

(Continued)

*Primary Examiner* — Joseph Stoklosa
(74) *Attorney, Agent, or Firm* — Muncy, Geissler, Olds & Lowe, PLLC (57) ABSTRACT

The disclosure relates to a load-adaptive bioelectrical current stimulator, which comprises a current output module, an adaptation module and a control module. The current output module generates a stimulus current to an electrode. The adaptation module detects the electrical status of the stimulus current passing through the electrode and generates a feedback signal to the control module. According to the feedback signal, the control module controls the current output module to stabilize the output status of the stimulus current adaptively. Thereby, the load-adaptive bioelectrical current stimulator can use the feedback control mechanism to regulate the value of the stimulus current to adapt to variation of load impedance.

4 Claims, 6 Drawing Sheets

(56) References Cited

OTHER PUBLICATIONS

Sivaprakasam, et al. "A Variable Range Bi-Phasic Current Stimulus Driver Circuitry for an Implantable Retinal Prosthetic Device", IEEE Journal of Solid-State Circuits, (Mar. 2005), pp. 763-771, vol. 40, No. 3.

Ghovanloo, et al. "A Compact Large Voltage-Compliance High Output-Impedance Programmable Current Source for Implantable Microstimulators IEEE Transactions on Biomedical Engineering", (Jan. 2005), pp. 97-105, vol. 52, No. 1.

Chen, et al. "Design of Stimulus Driver to Suppress Epileptic Seizure With Adaptive Loading Consideration" Next-Generation Electronics (ISNE) 2010 International Symposium, (Nov. 2010), pp. 9-12.

* cited by examiner

LOAD-ADAPTIVE BIOELECTRIC CURRENT STIMULATOR

BACKGROUND OF THE INVENTION

1. Field of the Invention

The present invention relates to a stimulator circuit, particularly to a bioelectric current stimulator circuit.

2. Description of the Related Art

The conventional bioelectric current stimulators may be categorized into two types. One type is disposed outside human bodies, and the other type is disposed inside human bodies, functioning as the auxiliary devices of sensory organs. One example of the former is a Taiwan patent No. I306407 "Device and Method for Generating Biomedical Electronic Signals". Examples of the latter include a U.S. Pat. No. 6,289,246 "High Compliance Output Stage for a Tissue Stimulator" and a U.S. Pat. No. 5,350,407 "Implantable Stimulator Having Quiescent and Active Modes of Operation".

In applications of the abovementioned stimulators to auxiliary devices of sensor organs, the load impedance ranges from tens of kΩ to hundreds of kΩ, depending on the contact points on the human or animal body. Even in the same contact point, the load impedance may also vary with the duration of contacting and the material of electrodes. Thus, the conventional stimulators cannot effectively output stimulus current when the load impedance is mismatched.

SUMMARY OF THE INVENTION

One objective of the present invention is to provide a load-adaptive bioelectric current stimulator, which uses a feedback control mechanism to regulate the stimulus current to adapt to variation of load impedance.

In one embodiment, the present invention proposes a load-adaptive bioelectric current stimulator, which comprises a current output module, an adaptation module and a control module. The current output module provides a stimulus current for an electrode. The adaptation module detects the electric status of the stimulus current passing through the electrode and generates a feedback signal to the control module. According to the feedback signal, the control module controls the current output module to stabilize the stimulus current adaptively. Thereby, the load-adaptive bioelectric current stimulator of the present invention can use the feedback mechanism to regulate the value of the stimulus current to adapt to the impedance variation of the load according to the special output status of the stimulus current.

In one embodiment, the adaptation module is an analog/digital conversion circuit. When the stimulus current passes through the electrode and generates an output voltage, the analog/digital conversion circuit provides the control module with a digital voltage signal functioning as a feedback signal according to the output voltage. In such a case, the control module is a digital control device. According to the digital voltage signal, the digital control device outputs an operating signal to the current output module in a PFM (Pulse Frequency Modulation) way to regulate the stimulus current. In one embodiment, the current output module includes a set of complementary current source circuits respectively receiving a set of complementary triggering signals of the operating signal to generate the stimulus current. The current source circuit includes a control circuit and a current mirror, wherein the control circuit is turned on/off by the corresponding triggering signal of the operating signal.

Thereby, the adaptation module can obtain the voltage signal of the stimulus current passing through the electrode and feedback a digital voltage signal to the control module, and the control module regulates the stimulus current output by the current output module to adapt to the impedance variation of the load.

In one embodiment, the adaptation module includes a current mirror and a comparator. The current mirror outputs a differential signal to the comparator according to the stimulus current. The comparator outputs an analog current signal functioning as the feedback signal to the control module according to the differential signal. In such a case, the control module is a charge pump system. According to the analog current signal, the control module controls the working voltage of the current output module and regulates the stimulus current in a PWM (Pulse Width Modulation) way. The current output module includes a control circuit and a current mirror, wherein the current mirror generates the stimulus current when the control circuit is triggered to operate.

Thereby, the adaptation module can obtain the current signal of the stimulus current passing through the electrode and feedback an analog current signal to the control module, and the control module regulates the stimulus current output by the current output module to adapt to the impedance variation of the load.

BRIEF DESCRIPTION OF THE DRAWINGS

To make easily understood the objectives, characteristics and advantages of the present invention, embodiments are described in detail in cooperation with the following drawings.

DETAILED DESCRIPTION OF THE INVENTION

Figure 1:
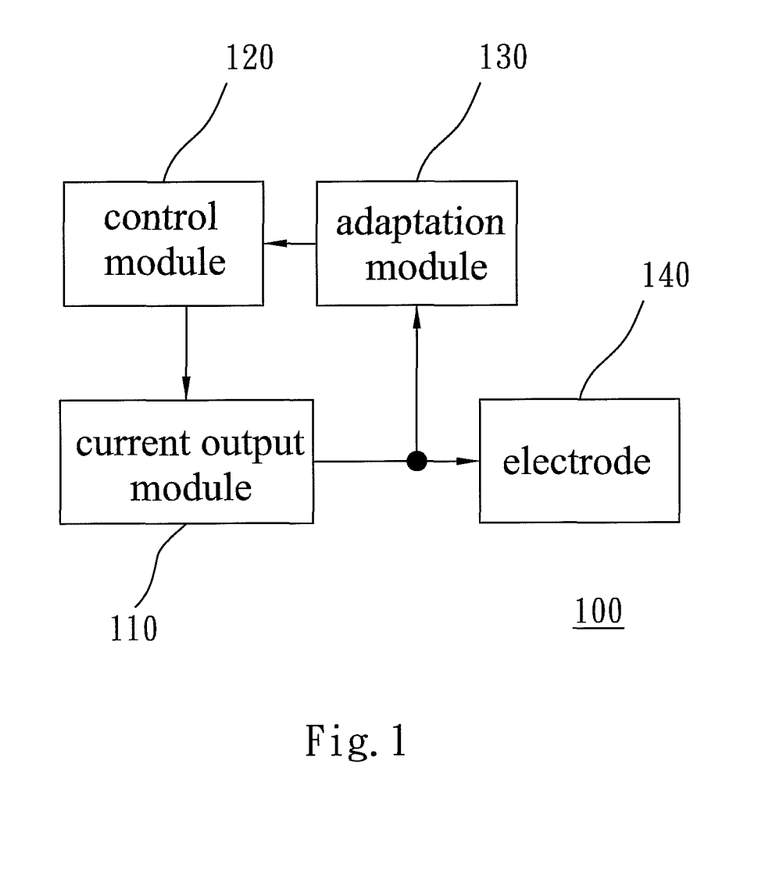
FIG. 1 a block diagram schematically showing the architecture of a load-adaptive bioelectric current stimulator according to one embodiment of the present invention.

Refer to FIG. 1 a block diagram schematically showing the architecture of a load-adaptive bioelectric current stimulator according to one embodiment of the present invention. The load-adaptive bioelectric current stimulator 100 of the present invention comprises a current output module 110, a control module 120 and an adaptation module 130. The current output module 110 provides a stimulus current for an electrode 140. The adaptation module 130 detects the electric status of the stimulus current passing through the electrode 140 and generates a feedback signal to the control module 120. According to the feedback signal, the control module 120 controls the current output module 110 to stabilize the stimulus current adaptively lest the stimulus current be influenced by the impedance variation of the load. Thereby, the load-adaptive bioelectric current stimulator 100 of the present invention can use the feedback mechanism to stabilize the stimulus current when the impedance varies with time and environment.

Figure 2:
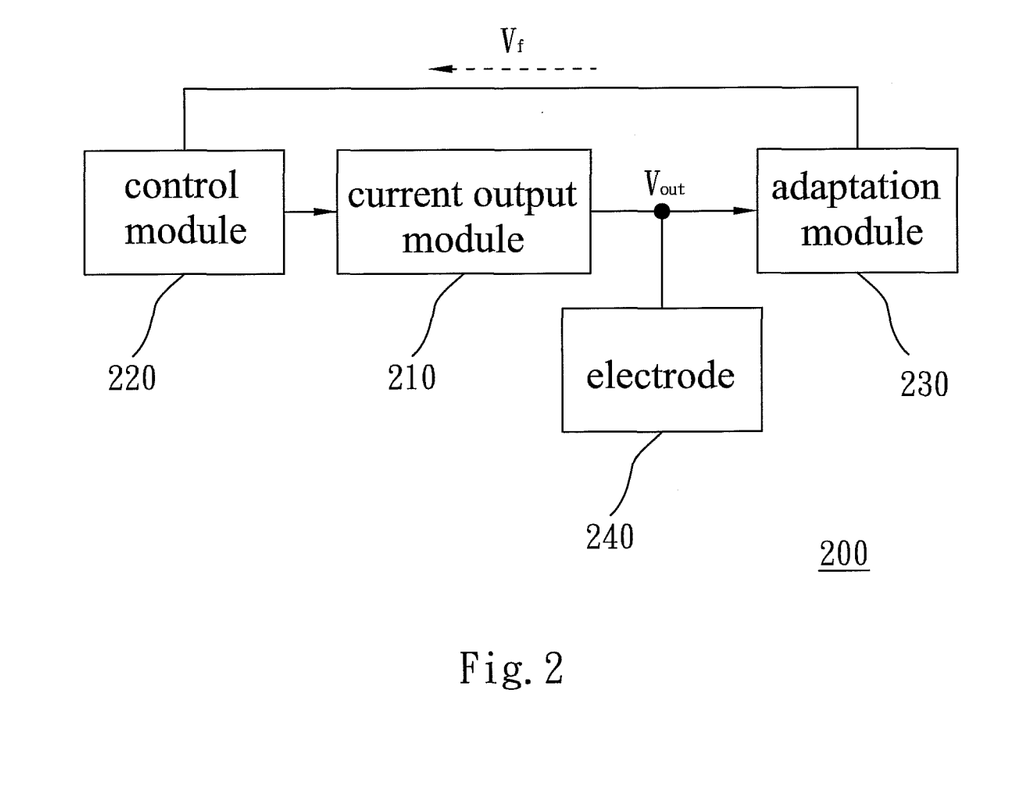
FIG. 2 a block diagram schematically showing one implementation of the load-adaptive bioelectric current stimulator 100 shown in FIG. 1 according to one embodiment of the present invention.

Refer to FIG. 2 a block diagram schematically showing one implementation of the load-adaptive bioelectric current stimulator 100 shown in FIG. 1 according to one embodiment of the present invention. In this embodiment, a voltage feedback mechanism and a digital control method are used to implement the load-adaptive bioelectric current stimulator 200. A voltage feedback mechanism is used between the adaptation module 230 and the current output module 210. When the stimulus current passes through the electrode 240, the adaptation module 230 detects the output $V_{out}$ and generates a feedback signal to the control module 220 according to the output voltage $V_{out}$. A digital control method is used between the control module 220 and the current output module 210, wherein the control module 220 provides an operating signal for the current output module 210, controlling the value of the stimulus current output by the current output module 210. Under the abovementioned two technologies, the adaptation module 230 is thus designed to generate a digital voltage signal functioning as a voltage feedback signal $V_f$ to the control module 220 in this embodiment.

Figure 3:
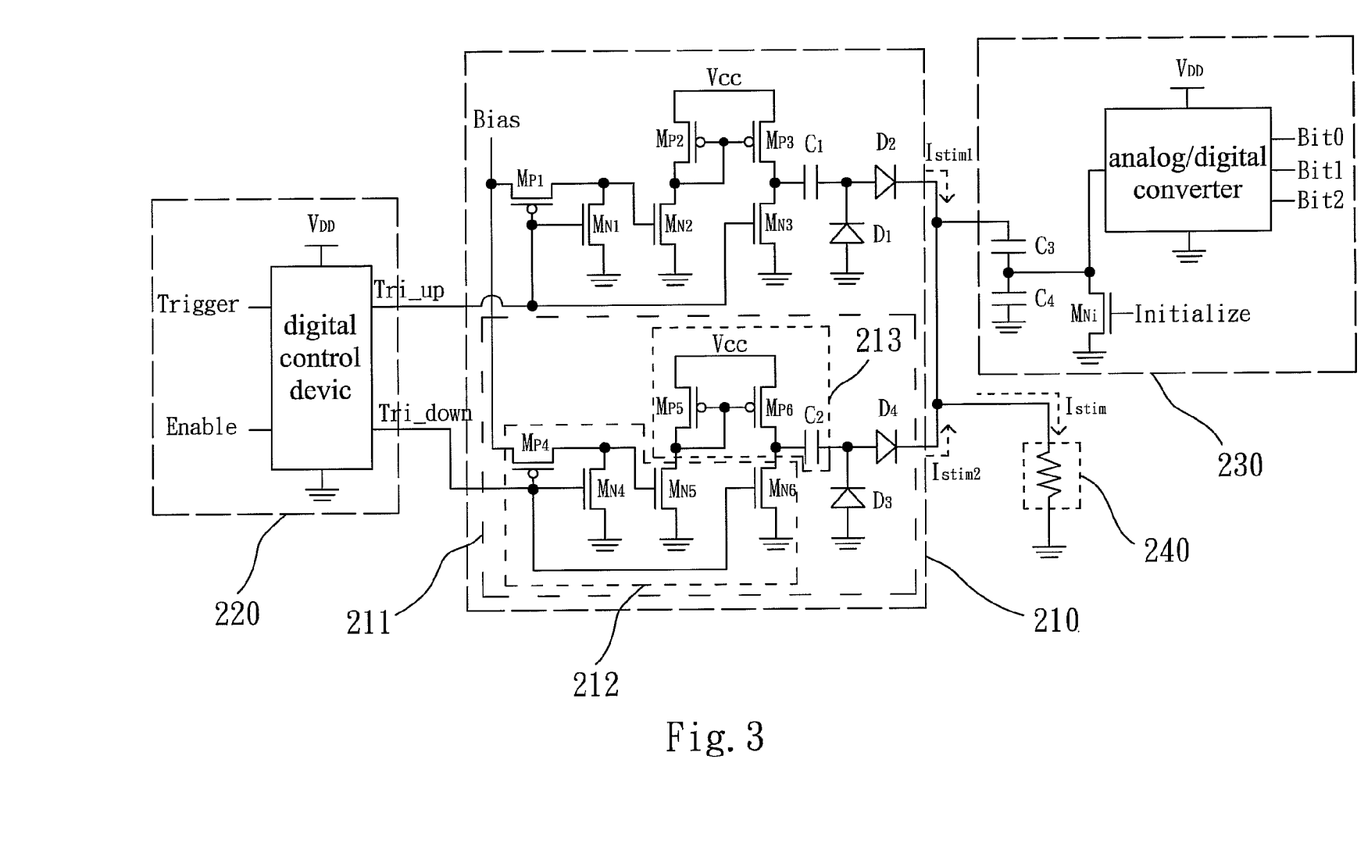
FIG. 3 a diagram showing the circuit of the load-adaptive bioelectric current stimulator 200 in FIG. 2 according to one embodiment of the present invention.

Refer to FIG. 3 a diagram showing the circuit of the load-adaptive bioelectric current stimulator 200 in FIG. 2 according to one embodiment of the present invention. In FIG. 3, the current output module 210 includes a set of complementary current source circuits. The upper current source circuit receives the up triggering signal (Tri_up) of the operating signal, and the lower current source circuit 211 receives the down triggering signal (Tri_down) of the operating signal. It should be noted: the upper current source circuit contributes a stimulus current component $I_{stim1}$, and the lower current source circuit 211 contributes a stimulus current component $I_{stim2}$. The sum of $I_{stim1}$ and $I_{stim2}$ is equal to the total stimulus current $I_{stim}$ output to the electrode 240. Via the instruction of this embodiment, the persons skilled in the art can easily design a current output module 210 containing three or more complementary current source circuits. In this embodiment, the timings of the triggering signals for different current source circuits are controlled to make the current source circuits generate stimulus current components at different time points, whereby is obtained the resultant stimulus current $T_{stim}$ required by different load states.

The current source circuit 211 includes a control circuit 212 and a current mirror 213. The control circuit 212 is turned on/off by the corresponding triggering signal of the operating signal, i.e. the down triggering signal Tri_down. When the control circuit 212 is turned on by the down triggering signal Tri_down, the current mirror 213 generates the stimulus component $I_{stim2}$. The control module 220 respectively provides the up triggering signal Tri_up and the down triggering signal Tri_down for the upper current source circuit and the lower current source circuit 211. When the up triggering signal Tri_up is at a low level $V_{SS}$, it turns on the upper current source circuit. Meanwhile, the down triggering signal Tri_down is at a high level $V_{DD}$ and turns off the lower current source circuit 211. In the upper current source circuit, when a transistor $M_{N2}$ is biased by a transistor $M_{P1}$, a transistor $M_{N3}$ is turned off. In such a case, the stimulus current component $I_{stim1}$ is transmitted by the current mirror, i.e. a transistor $M_{P2}$ and a transistor $M_{P3}$, and then passes a capacitor $C_1$ and a diode $D_2$. Simultaneously, the lower current source circuit 211 is at a discharging state. In such a case, a transistor $M_{N5}$ is turned off, and a transistor $M_{N6}$ is turned on; a capacitor $C_2$, which has been charged in the last operating cycle, discharges via the transistor $M_{N6}$ and a diode $D_3$.

In another operating cycle, when the lower current source circuit 211 is turned on by the down triggering signal Tri_down, the up triggering signal Tri_up is at a high level $V_{DD}$, and the down triggering signal Tri_down is at a low level $V_{SS}$. In such a case, the transistor $M_{N2}$ of the control circuit 212 is turned off, and the transistor $M_{N3}$ of the control circuit 212 is turned on. Thus, the capacitor $C_1$, which has been charged, discharges via the transistor $M_{N3}$ and the diode $D_1$. Meanwhile, the lower current source circuit 211 is at a working state, and the stimulus current component $I_{stim2}$ is transmitted by the current mirror 213 that consists of a transistor $M_{P5}$ and a transistor $M_{P6}$ and then passes the capacitor $C_2$ and a diode $D_4$. During the operation interruption of the current output module 210, the up triggering signal Tri_up and the down triggering signal Tri_down are at a high level $V_{DD}$, and the gates of the transistor $M_{N2}$ and the transistor $M_{N5}$ are at a low level $V_{SS}$ and turned off. Thus, no stimulus current $I_{stim}$ is transmitted.

In one embodiment, the adaptation module 230 is an analog/digital conversion circuit. The adaptation module 230 obtains the voltage signal of the stimulus current $I_{stim}$, which passes through the load 240, via a capacitor $C_3$ and a capacitor $C_4$ and then uses an analog/digital converter to generate a digital feedback voltage signal Bit 0, Bit 1 or Bit 2. In such a case, the control module is a digital control device. The digital feedback signal is used as a triggering signal Trigger. The triggering signal Trigger together with an enabling signal Enable of the bioelectric current stimulator is used to implement a PFM control activity, whereby to generate an operating signal containing a plurality of triggering signals required by the current source circuits, such as the up triggering signal Tri_up and the down triggering signal Tri_down.

Figure 4:
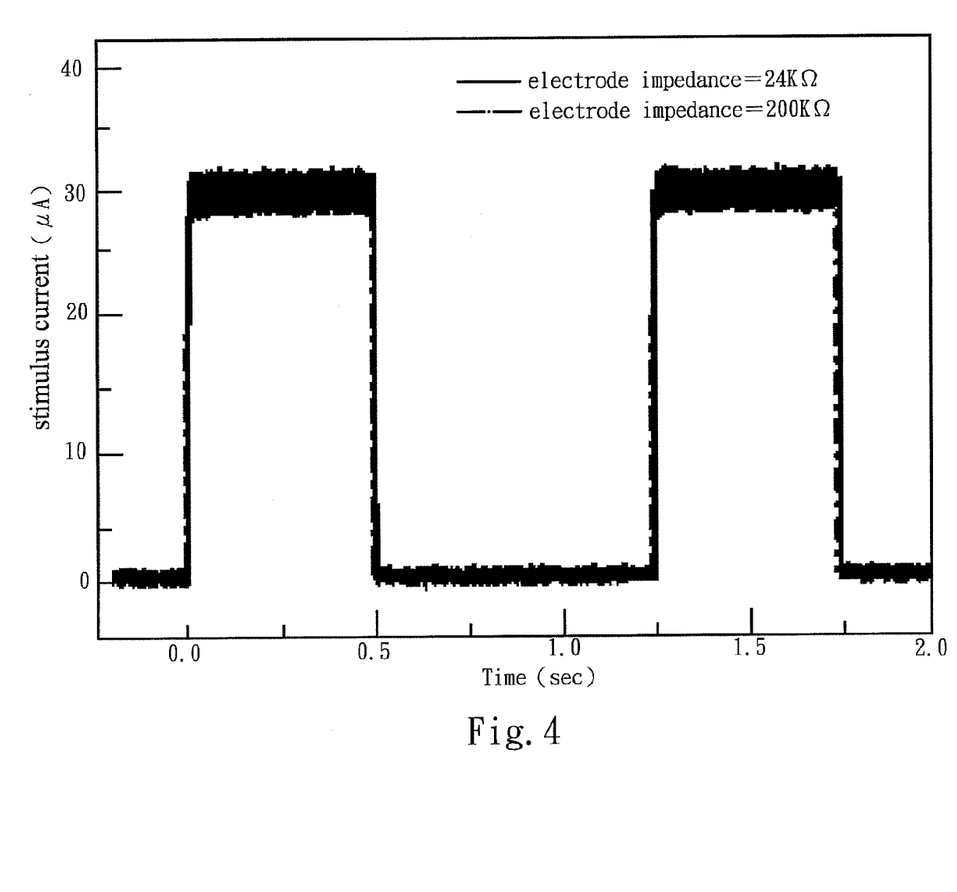
FIG. 4 a diagram showing the waveforms of a bioelectric current stimulator according to one embodiment of the present invention.

Refer to FIG. 4 for the waveforms of a bioelectric current stimulator according to one embodiment of the present invention. The equivalent impedance of the electrode 240 may vary from 20 to 200Ω with time, tissues, or materials. However, the stimulus current $I_{stim}$ should not vary anyway. The bioelectric current stimulator shown in FIG. 3 provides 30 μA stimulus current stably and thus can indeed overcome the problem of the conventional technology.

Figure 5:
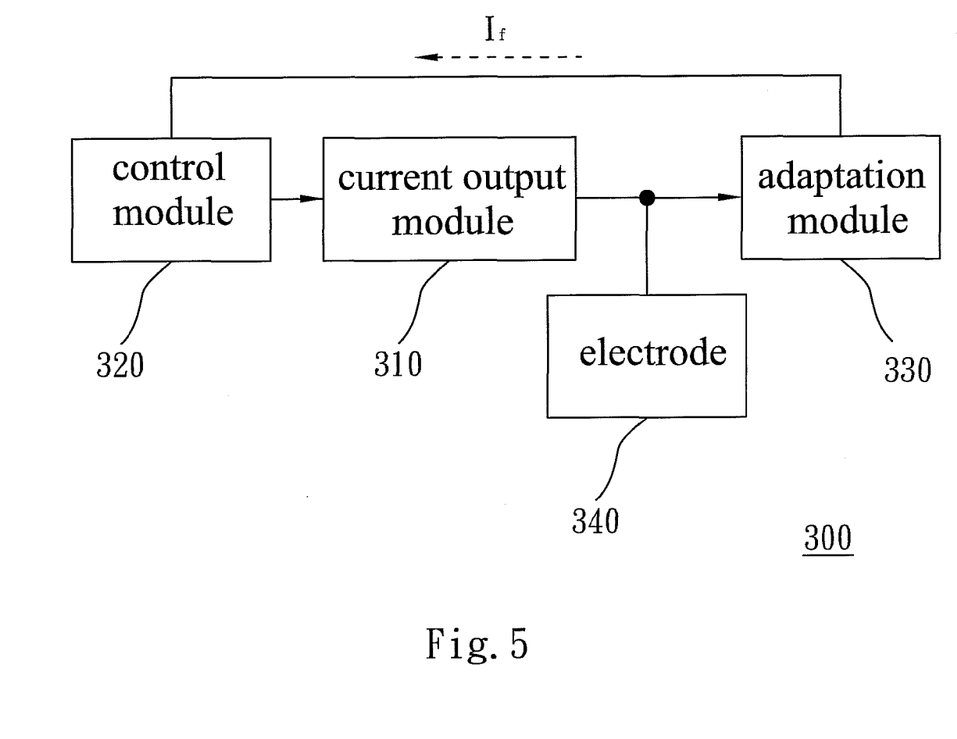
FIG. 5 a block diagram schematically showing another implementation of the load-adaptive bioelectric current stimulator 100 shown in FIG. 1 according to one embodiment of the present invention.

Refer to FIG. 5 a block diagram schematically showing another implementation of the load-adaptive bioelectric current stimulator 100 shown in FIG. 1 according to one embodiment of the present invention. In this embodiment, a current feedback mechanism and an analog control method are used to implement the load-adaptive bioelectric current stimulator 300. A current feedback mechanism is used between the adaptation module 330 and the current output module 310. When the stimulus current passes through the electrode 340, the adaptation module 330 detects the output current and generates a feedback signal to the control module 320 according to the output current. The adaptation module 330 may detect the output current via a Helmholtz core or a pair of electrodes 340 that form a current loop. Moreover, an analog control method is used between the control module 320 and the current output module 310. For example, the control module 320 directly controls the value of the stimulus current of the current output module 310.

The control module 320 generates a working voltage to the current output module 310 according to the enabling signal En of the bioelectric current stimulator. The current output module 310 generates a stimulus current to the electrode 340 according to the enabling signal En. The adaptation module 330 detects the value of the stimulus current that has been influenced by the impedance matching of the electrode 340 and generates an analog current signal functioning as a feedback current signal $I_f$ to the control module 320. Thereby, the control module 320 modifies the working voltage according to the value of the stimulus current to overcome the influence of the impedance variation of the electrode 340. Thus is stabilized the stimulus current. According to the instructions shown in FIG. 2 and FIG. 5, the persons having ordinary knowledge of the art should be able to choose an appropriate feedback mechanism and design a corresponding control method for the bioelectric current stimulator of the present invention.

Figure 6:
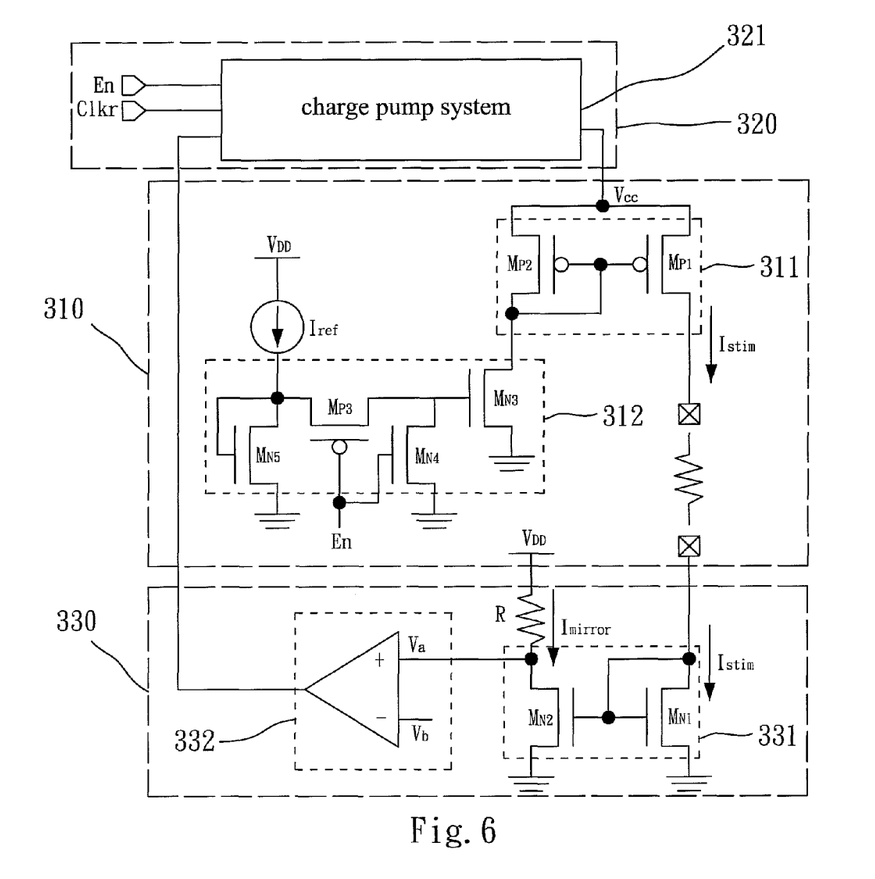
FIG. 6 a diagram showing the circuit of the load-adaptive bioelectric current stimulator 300 in FIG. 5 according to one embodiment of the present invention.

Refer to FIG. 6 a diagram showing the circuit of the load-adaptive bioelectric current stimulator 300 in FIG. 5 according to one embodiment of the present invention. In FIG. 6, there is a pair of electrodes 340 forming a current loop. The current output module 310 includes a current mirror 311 and a control circuit 312. The enabling signal En turns on/off the control circuit 312. When the control circuit 312 is turned on, the current mirror 311 generates a stimulus current $I_{stim}$. It should be noted that the working voltage $V_{CC}$ of the current mirror 311 is directly controlled by the control module 320. When the control module 320 adjusts the working voltage $V_{CC}$ according to the feedback signal, the value of the stimulus current $I_{stim}$ is also adjusted correspondingly. In details, when the enabling signal En turns on the transistor $M_{P3}$ and turns off the transistor $M_{N4}$, the transistor $M_{N3}$ is turned on to make the current mirror 311 generate a stimulus current $I_{stim}$. When the enabling signal En turns off the transistor $M_{P3}$ and turns on the transistor $M_{N4}$, the transistor $M_{N3}$ is turned off to make the current mirror 311 unable to generate a stimulus current $I_{stim}$.

The adaptation module 330 includes a current mirror 331 and a comparator 332. The current mirror 331 generates a mirrored current $I_{mirror}$ according to the stimulus current $I_{stim}$. Via a resistor R, the mirrored current $I_{mirror}$ generates an electric potential $V_a$ to the comparator 332. The comparator 332 further obtains a reference potential $V_b$. Thus, the potential $V_a$ and the potential $V_b$ form a differential signal. According to the differential signal, the comparator 332 generates an analog current signal functioning as a feedback current signal $I_f$. In one embodiment, the control module 321 is a charge pump system. According to the enabling signal En and clock signal Clkr that control the bioelectric current stimulator and the analog current signal, the charge pump system performs a PWM control activity to control the working voltage $V_{CC}$ of the current mirror 311 of the current output module 310. Thus, the feedback control mechanism of the bioelectric current stimulator of the present invention can offset the time- and environment-dependent impedance variation of the load.

The embodiments described above are only to exemplify the present invention but not to limit the scope of the present invention. Any equivalent modification or variation made by the persons skilled in the art according to the spirit of the present invention is to be also included within the scope of the present invention.

What is claimed is:

1. A load-adaptive bioelectric current stimulator comprising:
   a current output module generating a stimulus current to an electrode;
   an adaptation module detecting an electric status of said stimulus current when said stimulus current passes through said electrode, and generating a feedback signal; and
   a control module controlling said current output module according to said feedback signal to stabilize output of said stimulus current adaptively,
   wherein said adaptation module includes:
      a current mirror; and
      a comparator,
         wherein said current mirror of said adaptation module generates a differential signal of voltage difference to said comparator according to said stimulus current, and
   wherein said comparator generates an analog current signal to said control module as said feedback signal according to said differential signal of voltage difference, and said stimulus current directs to ground through said current mirror of said adaptation module.

2. The load-adaptive bioelectric current stimulator according to claim 1, wherein said control module is a charge pump system, and according to said analog current signal, said charge pump system controls a working voltage output by said current output module in a PWM (Pulse Width Modulation) way to regulate said stimulus current.

3. The load-adaptive bioelectric current stimulator according to claim 2, wherein said current output module includes a control circuit and a current mirror of said current output module, and when said control circuit is activated, said current output module generates said stimulus current via said current mirror of said current output module.

4. A load-adaptive bioelectric current stimulator, comprising:
   a current output module generating a stimulus current to an electrode;
   an adaptation module detecting an electric status of said stimulus current when said stimulus current passes through said electrode, and generating a feedback signal; and
   a control module controlling said current output module according to said feedback signal to stabilize output of said stimulus current adaptively,
   wherein said adaptation module is an analog/digital conversion circuit, and said analog/digital conversion circuit provides a digital voltage signal for said control module as said feedback signal according to an output voltage generated by said stimulus current when said stimulus current passes through said electrode,
   wherein said control module is a digital control device, and according to said digital voltage signal, said digital control device provides said current output module with an operating signal composed of a set of complementary triggering signals in a PFM (Pulse Frequency Modulation) way to regulate said stimulus current,
   wherein said current output module includes a set of complementary current source circuits receiving said set of complementary triggering signals of respectively and generating said stimulus current, and said stimulus current directs to ground through said electrode, and
   wherein each of said set of complementary current source circuits includes a control circuit and a current mirror, and said control circuit is turned on/off by a corresponding one of said set of complementary triggering signals.

* * * * *